(12) United States Patent
Terebesi et al.

(10) Patent No.: US 8,671,945 B2
(45) Date of Patent: Mar. 18, 2014

(54) LOW-DOSE TRANSDERMAL PATCHES WITH HIGH DRUG RELEASE

(75) Inventors: Ildiko Terebesi, Berlin (DE); Christian Zurth, Berlin (DE); Hannes-Friedrich Ulbrich, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 172 days.

(21) Appl. No.: 13/225,829

(22) Filed: Sep. 6, 2011

(65) Prior Publication Data

US 2012/0073578 A1 Mar. 29, 2012

(30) Foreign Application Priority Data

Sep. 6, 2010 (EP) .................................. 10175498
Feb. 22, 2011 (EP) .................................. 11155469

(51) Int. Cl.
*A61F 6/06* (2006.01)
(52) U.S. Cl.
USPC .......................................... 128/832; 602/41
(58) Field of Classification Search
USPC ...................................... 602/41–54; 128/832
See application file for complete search history.

(56) References Cited

U.S. PATENT DOCUMENTS

| | | | |
|---|---|---|---|
| 4,913,905 A | 4/1990 | Fankhauser et al. | |
| 5,128,124 A | 7/1992 | Fankhauser et al. | |
| 6,074,665 A * | 6/2000 | Horstmann et al. | 424/449 |
| 6,440,454 B1 | 8/2002 | Santoro et al. | |
| 6,902,741 B1 * | 6/2005 | Grawe et al. | 424/448 |
| 8,110,565 B2 * | 2/2012 | Houze et al. | 514/183 |
| 2005/0055975 A1 | 3/2005 | Tackett et al. | |
| 2005/0142175 A1 * | 6/2005 | Langguth et al. | 424/449 |
| 2005/0175678 A1 | 8/2005 | Breitenbach et al. | |
| 2006/0251707 A1 | 11/2006 | Schumacher et al. | |
| 2010/0086582 A1 | 4/2010 | Tang et al. | |
| 2011/0165247 A1 | 7/2011 | Breitenbach et al. | |

FOREIGN PATENT DOCUMENTS

| | | |
|---|---|---|
| CA | 2 548 739 | 6/2005 |
| CA | 2 605 112 | 11/2006 |
| EP | 0 285 563 | 10/1988 |
| EP | 1 541 137 | 6/2005 |
| WO | WO-99 66908 | 12/1999 |
| WO | WO-2004 058247 | 7/2004 |
| WO | WO-2005 055975 | 6/2005 |
| WO | WO-2005 058287 | 6/2005 |
| WO | WO-2006 117139 | 11/2006 |
| WO | WO-2010 042152 | 4/2010 |

OTHER PUBLICATIONS

International Search Report for PCT/EP2011/065261 dated Jun. 19, 2012.
International Search Report for PCT/EP2011/065204 dated Nov. 28, 2011.

* cited by examiner

*Primary Examiner* — Michael A. Brown
(74) *Attorney, Agent, or Firm* — Millen, White, Zelano & Branigan, P.C.

(57) ABSTRACT

The present invention relates to the field of pharmaceutical formulation techniques. The invention provides a low dosage pharmaceutical composition for transdermal delivery of hormones, preferably a progestin, such as a Gestodene, and an estrogen, preferably Ethinylestradiol so as to achieve plasma concentration profiles effective in inhibiting ovulation in a woman.

25 Claims, 1 Drawing Sheet

LOW-DOSE TRANSDERMAL PATCHES WITH HIGH DRUG RELEASE

FIELD OF INVENTION

The present invention relates to the field of pharmaceutical formulation techniques. The invention provides a low dosage pharmaceutical composition for transdermal delivery of hormones, preferably a progestin, such as a Gestodene, and an estrogen, preferably Ethinylestradiol so as to achieve plasma concentration profiles effective in inhibiting ovulation in a woman.

BACKGROUND

Transdermal delivery of estrogens and progestins for providing contraception is a known concept (Sitruk-Ware, Transdermal application of steroid hormones for contraception, J Steroid Biochem Molecul Biol, Volume 53, p 247-2511). It is also known that estrogens and progestins do generally poorly penetrate the skin, for which reason it is common, to incorporate agents with skin penetrating enhancing effect in transdermal systems.

ORTHO EVRA® is the first transdermal contraceptive patch which received the approval from the Marketing Authorities. It was launched at first in the US in 2002. ORTHO EVRA® is a once-a-week transdermal contraceptive system with a size of 20 cm$^2$ and comprises 6 mg Norelgestromin and 0.75 mg Ethinylestradiol.

ORTHO EVRA® is a thin, matrix-type transdermal contraceptive patch consisting of three layers. The backing layer is composed of a beige flexible film consisting of a low-density pigmented polyethylene outer layer and a polyester inner layer. It provides structural support and protects the middle adhesive layer from the environment. The middle layer contains polyisobutylene/polybutene adhesive, crospovidone, non-woven polyester fabric and lauryl lactate as inactive components. The active components in this layer are the hormones, Norelgestromin and Ethinylestradiol. The third layer is the release liner, which protects the adhesive layer during storage and is removed just prior to application. It is a transparent polyethylene terephthalate (PET) film with a polydimethylsiloxane coating on the side that is in contact with the middle adhesive layer.

AG200-15, the lead contraceptive patch developed by Agile Therapeutics, is currently under investigation in a Phase 3 study to evaluate the efficacy and safety. AG200-15 is designed to effectively deliver 25-30 µg estrogen (Ethinylestradiol) and 100-120 µg Levonorgestrel in a weekly regime for 21 days. The patch is applied once weekly for three weeks followed by a patch-free week.

A transdermal contraceptive patch comprising Gestodene in combination with an estrogen is not yet on the market.

However, there are a number of publications describing compositions for the transdermal delivery of Gestodene.

Gestodene itself is a known orally active synthetic progestin with a progesterone-like profile of activity (see, U.S. Pat. No. 4,081,537). It is used as an oral contraceptive in combination with certain estrogens.

U.S. Pat. No. 5,512,292 is directed to compositions comprising a contraceptive effective amount of Gestodene and an estrogen, such as Ethinylestradiol, together with a suitable permeation enhancer. The amount of the estrogen co-delivered is kept at a constant and contraceptive effective rate while the amount of Gestodene co-delivered varies depending on the phase of the menstrual cycle.

In U.S. Pat. No. 5,376,377 comparable studies between transdermal systems with and without penetration enhancers are shown. The studies include an adhesive layer made of ethylene vinyl acrylate and as the active ingredient, Gestodene and an estrogen (Ethinylestradiol). The study results indicate the need of incorporation of penetration enhancers in the adhesive layer so as to achieve contraceptive effective amounts. Maximal plasma levels of about 0.8 ng/mL were achieved.

WO 90/04397 also discloses examples of compositions for transdermal delivery of Gestodene, optionally in combination with an estrogen, such as Ethinylestradiol, wherein the composition further may comprise a penetration enhancer, such as 1,2-propandiol or isopropylmyristate. A number of various polymers are mentioned as adhesive layer. Examples on polar polymers (polyacrylates and silicones) in combination with a penetration enhancer are specifically disclosed. The resulting plasma levels of Gestodene at steady state conditions were approximately 250 to 337 pg/mL.

In U.S. Pat. No. 6,521,250 is disclosed an adhesive layer that comprises a mixture of styrene-isoprene block copolymer and a hydrogenated resin acid or its derivatives, the amount of the resin being of 55-92%. Such an adhesive layer seems suitable for the transdermal delivery of Estradiol in combination with a progestin in that such systems have a proper adhesive contact with the skin for long-term application and prevent crystallization of the hormones.

U.S. Pat. No. 5,904,931 relates to transdermal therapeutic systems containing in the drug-containing layer a steroid (such as Gestodene) and dimethyl isosorbide. The latter enhances the solubility of the steroid in the drug-containing layer. The concentration of the Gestodene in the drug-containing layer may vary from 1-40% by weight of the layer and the drug-containing layer may consist of adhesives such as polyacrylates, silicones, styrene-butadiene copolymers and polyisobutylenes. Especially, polar polymers such as polyacrylates, are suitable.

DE 199 06 152 relates to a transdermal drug delivery system in which Gestodene is embedded in a polar polymer, such as polyvinylpyrrolidone, methylcellulose, ethylcellulose, and hydroxypropylcellulose, previous to being added to an adhesive polymer, such as polyisobutylene. Thus, this transdermal drug delivery system is a two-phase system and the drug-containing layer is not transparent because of the content of the polar polymers, which upon exposure to water will result in the presence of milky-white spots. The amount of Gestodene in the drug-containing layer is 5.1% by weight of the drug-containing layer.

WO 02145701 describes a TTS (Transdermal Therapeutic System) which is suitable for steroids (Gestodene). Gestodene may be incorporated in the adhesive layer in an amount substantially at or near or even above the saturation with respect to their concentration in the carrier composition rather than substantially at subsaturation. Preferably, the amount of the steroid is from about 0.1% to about 6% by weight, based on the dry weight of the total carrier composition. The adhesive layer may include all non-toxic natural and synthetic polymers known and which are suitable for use in transdermal systems, for example polyacrylates, polysiloxanes, polyisobutylenes, styrene block copolymers and the like.

WO 92/07590 discloses compositions with penetration enhancers for the transdermal delivery of Gestodene and an estrogen so as to achieve maximal plasma levels of Gestodene of about 0.9 ng/mL. The amounts of the estrogen and of Gestodene are described that are present in the therapeutic device, and that are required to achieve a contraceptive effect, depend on many factors, such as the minimum necessary dosage of each drug; the permeability of the matrix, of the adhesive layer and of the rate-controlling membrane, if present; and the period of time for which the device will be fixed to the skin.

Since the drugs are to be released over a period of more than one day, there is, in fact, no upper limit to the maximum amounts of the drugs present in the device. The minimum amount of each drug is determined by the requirement that sufficient quantities of drug must be present in the device to maintain the desired rate of release over the given period of application.

Drug amounts or ranges of amounts are not mentioned in WO 92/07590.

So far the minimum amount of each drug, i.e. Gestodene and estrogen, to maintain the desired release rate over a defined period of administration is not clearly known.

EP 1 541 137 describes pharmaceutical compositions for transdermal delivery comprising a drug-containing layer that comprises Gestodene or an ester thereof and a carrier selected from the group consisting of polyisobutylenes, polybutenes, polyisoprenes, polystyrenes, styrene isoprene styrene block polymers, styrene butadiene styrene block polymers and mixtures thereof, wherein the drug-containing layer has a solubility for said Gestodene of no more than 3% by weight of the drug-containing layer, and wherein the Gestodene or an ester thereof is present in an amount ranging between 0.5 and 3% by weight of the drug-containing layer.

The Gestodene drug plasma levels after application of a composition which is a 10 cm$^2$ patch comprising 0.9 mg Ethinylestradiol and 1.9 mg Gestodene is 2082 pg/mL ($C_{max}$.) whereas a 10 cm$^2$ patch comprising 0.67 mg Ethinylestradiol and 1.33 mg Gestodene reaches 1995 pg/mL ($C_{max}$.) when applied as single dose.

EP 1 541 137 also demonstrates that a drug-containing layer of a polar polymer (polyacrylate) requires a concentration of Gestodene of 3.9% by weight of this layer to achieve the desired high release rate. Additionally, it is shown that the same high release rate can be achieved with a concentration of 1.9% by weight of Gestodene in a drug-containing layer comprising a less polar polymer, such as polyisobutylene.

Even EP 1 541 137 does not disclose the minimum amount of each drug, i.e. Gestodene and estrogen, to maintain the desired release rate over a defined period of administration.

SUMMARY OF THE INVENTION

This invention relates to compositions suitably formulated for transdermal delivery of hormones, so that contraceptive effective levels are achieved. The actual hormones are preferably steroidal hormones, such as progestins, such as a Gestodene, which optionally may be used in combination with an estrogen. The preferred estrogen is Ethinylestradiol. The provided transdermal systems comprise a limited number of ingredients. For example penetration enhancers and or permeation enhancers are not required in order to achieve high release rate and therapeutically effective plasma levels.

Thus, the present inventors have found, unlike what could be expected, that the use of a small but constant amount of Ethinylestradiol in combination with varying amounts of Gestodene in a transdermal patch results in increasing daily release rates of Ethinylestradiol in direct correlation to the decreasing amounts of Gestodene in the transdermal delivery composition, as shown by the series of experiments herein using a constant amount of Ethinylestradiol in combination with decreasing amounts of Gestodene. Gestodene release relative to its concentration in the formulation was also increased. This resulted in increased plasma levels for Ethinylestradiol and almost constant plasma levels of Gestodene for specific formulations with constant Ethinylestradiol content and decreased Gestodene content.

It is commonly known that the solubility for the steroidal hormone (i.e. Gestodene) is critical for the successful achievement of therapeutically effective levels of a hormone in the blood. It is also known that drug-containing adhesive layers containing the more non-polar type of polymer such as the polyisobutylene in preference to the polyacrylates are better in terms of achieving high plasma AUC (EP 1 541 137, Example 4).

It has been discovered that transdermal therapeutic systems with drug-containing layers, preferably containing a nonpolar polymer, such as a polyisobutylene, and characterized by having a limited solubility with respect to Gestodene of no more than 3% by weight, have a high release rate of Gestodene despite that the actual load of Gestodene in the drug-containing layer is low.

It was therefore an object of the invention to provide transdermal compositions comprising low amounts of Gestodene and Ethinylestradiol in a polyisobutylene-containing adhesive matrix with sufficient release rates of drugs to achieve a therapeutically effective plasma level, i.e., to inhibit the ovulation of healthy women.

This is achieved by the innovative transdermal composition comprising Ethinylestradiol in an amount of from about 0.5% by weight of the drug-containing layer in a polyisobutylene-containing adhesive matrix with varying amounts of Gestodene. Gestodene is present in the polyisobutylene-containing adhesive matrix in an amount of from about 0.4 to 1.95% by weight of the drug-containing layer, preferably of from about 0.9 to 1.5% by weight of the drug-containing layer.

That means that the innovative transdermal composition delivers Ethinylestradiol with higher release rates by using a matrix having a constant amount of Ethinylestradiol and lower amounts of Gestodene.

The present invention is a selection invention within EP 1 5141 137 which discloses compositions for transdermal delivery with Gestodene amounts of from about 0.5 to 3% by weight of the drug-containing layer, preferably 1 to 2% by weight of the drug-containing layer.

EP 1 5141 137 discloses that the composition may optionally comprise an estrogen. The estrogen is present in amounts of from about 0.5 to 10% by weight of the drug-containing layer, preferably 0.75 to 5% by weight of the drug-containing layer, more preferably 1 to 3% by weight of the drug-containing layer and most preferably 1 to 2% by weight of the drug-containing layer.

According to EP 1 5141 137 the term "estrogen" includes both the natural 17β-estradiol and the semi-synthetic estrogen derivatives such as esters of natural estrogen and 17-alkylated estrogens. Semi-25 synthetic esters of natural estrogen include for example estradiol-17-β-enanthate, estradiol-17-β-valerate, estradlol-17-β-benzoate, estradlol-17-β-undecanoate, estradiol-16,17-hemlsuccinate or estradiol-17-β-cyplonate. Examples on 17-alkylated estrogens are Ethinylestradiol, Ethinylestradiol-3-isopropylsulphonate, quinestrol, mestranol or methylestradiol. The term "estrogen" may also include a non-steroidal compound having estrogen activity, such as diethylstilbestrol, dienestrol, clomifen, chlorotrianesene or cyclofenil. In a preferred embodiment, the estrogen is Ethinylestradiol.

EP 1 5141 137 discloses that Gestodene and optionally the estrogen are present in a pharmaceutically acceptable carrier which contains at least one polymer selected from the group consisting of polyisobutylenes, polybutenes, polyisoprenes, polystyrenes, styrene isoprene styrene block polymers, styrene butadiene styrene block polymers and mixtures thereof.

After the administration of the transdermal therapeutic system according to the invention comprising low amounts of Gestodene as defined above in combination with low and constant amounts of Ethinylestradiol, plasma levels of Gestodene were observed from the released drug amount of the drug-containing layer, which are surprisingly almost in the same range as for the 1.9% by weight of the drug-containing layer transdermal composition embodiment described in EP 1 541 137.

Simultaneously, the plasma levels of Ethinylestradiol are clearly increased after the administration of a transdermal therapeutic system according to the invention.

This is clearly an advantage over the previously known transdermal therapeutic system in terms of decreasing the risk of skin irritation, decreasing the exposure of hormone to the user and to the environment as well as saving costs for manufacturing such transdermal compositions with a lower amount of active.

Accordingly, a first aspect of the Invention relates to compositions for transdermal delivery of Gestodene and Ethinylestradiol. The composition comprises a drug-containing layer comprising said Gestodene and Ethinylestradiol in a polyisobutylene-containing adhesive matrix, and the drug-containing layer having solubility for Gestodene of no more than 3% by weight of the drug-containing layer.

In a particular aspect thereof, the invention relates to a composition comprising Gestodene and Ethinylestradiol in polyisobutylene where polyisobutylene is present in an amount of from about 15 to 99% by weight of the drug-containing adhesive layer.

In another particular aspect thereof, the invention relates to compositions comprising a drug-containing adhesive layer comprising Gestodene and Ethinylestradiol, polyisobutylene in an amount of from about 15 to 99% by weight of the drug-containing layer, a tackifier, such as a rosin ester in an amount of up to 85% by weight, such as in an amount in the range of 1 to 85% of the drug-containing layer.

In a still particular aspect, the invention relates to a composition for transdermal delivery comprising a polyisobutylene-containing adhesive matrix that comprises 0.3 to 2.5 mg Gestodene, preferably 0.5 to 2.3 mg Gestodene, more preferably 1 to 2.1 mg Gestodene. Special compositions contain for instance In another particular aspect, the invention relates to a composition for transdermal delivery comprising a polyisobutylene-containing adhesive matrix that comprises and 0.1 to 0.9 mg Ethinylestradiol, preferably 0.3 to 0.6 mg Ethinylestradiol, most preferably 0.55 mg Ethinylestradiol.

It has surprisingly been found that relatively high plasma levels of Gestodene can be maintained for a prolonged period of time by administering varying amounts of Gestodene with formulations according to the invention. The plasma profile and plasma levels of Gestodene, as resulting from the administration of Gestodene and Ethinylestradiol, are effective in inhibiting the ovulation in a woman.

Therefore compositions of the invention may be used for inhibiting ovulation or alternatively for the treatment of endometriosis, pre-menstrual syndrome, climacteric disorders, prevention of osteoporosis, regulating the menstrual cycle or stabilizing the menstrual cycle.

When the composition is administered, then a plasma concentration-time curve of Gestodene is achieved characterized by having plasma levels of Gestodene and Ethinylestradiol in a concentration exceeding the value predicted from a linear extrapolation based on the plasma levels achieved with a formulation containing 1.9% Gestodene and 0.9% Ethinylestradiol in the polymer matrix at a patch size of 10 $cm^2$, thus having a content of 1.9 mg Gestodene and 0.9 mg Ethinylestradiol. In association herewith, the invention relates to a method for inhibiting ovulation in a female, such as a woman.

Similar findings were observed when the formulations were investigated in an in vitro-dissolution test. The formulations of the invention surprisingly provide a non-linear relationship between drug content and the resulting in-vitro release rates for Gestodene, when its concentration in the polymer matrix was decreased. More specifically, a decrease in Gestodene content also results in increased Ethinylestradiol in-vitro release, although the concentration of Ethinylestradiol in all formulations was kept constant. For Gestodene only a slightly decreased in-vitro release was observed in contrast to the expected linear relationship.

The expectation with respect to the investigation of patches with varying drug content of Gestodene were, that a decrease in Gestodene content in the patch matrix will decrease the amount of released Gestodene proportionally, whereas the amount of Ethinylestradiol released will remain unchanged, as the Ethinylestradiol content in the patch matrix was kept constant. The theoretically expected and practically found release rates of Ethinylestradiol and Gestodene from the different patch formulations are summarized in Table 3 and FIG. 2.

Thus, the skilled person will be able to deduce from Table 3 the size and active ingredient contents that are required to achieve specific desired in-vitro release rates and thus desired plasma profiles.

A dosage unit comprises a drug-containing adhesive layer made of polyisobutylene comprising Gestodene in combination with Ethinylestradiol with amounts of the above-defined ranges and one or more pharmaceutically acceptable excipients or carriers, wherein the drug-containing layer has solubility with respect to Gestodene of no more than 3% by weight of the drug-containing layer.

DETAILED DESCRIPTION

Figure 1:
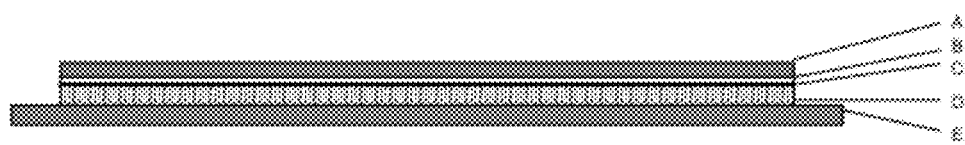
FIG. 1 shows the structure of an embodiment of the patch in cross section:
A covering film (=backing layer),
B adhesive layer with UV absorber,
C separation layer,
D active-ingredient-containing adhesive layer,
E siliconized or fluorine-coated removable film (release liner)

The invention provides compositions for transdermal delivery of hormones (transdermal therapeutic system) that upon topical application to the skin or to a mucosa results in therapeutically effective amounts, such as contraceptive effective amounts of the hormones Gestodene and Ethinylestradiol. Skin penetration enhancers are not necessarily incorporated in the drug-containing layer.

As used herein, the term "topical" or "topically" denotes the direct contact of the composition with a surface area of a mammal including skin. The compositions of the invention may be designed in several various application forms provided that the composition comprises a drug-containing adhesive layer, which is adapted to be placed near to or in direct contact with skin or mucosa upon topically administering the composition.

Therefore, in a preferred application form, the composition, e.g. the transdermal therapeutic system, consists essentially of
a) a backing layer;
b) at least one drug-containing layer comprising Gestodene and Ethinylestradiol in a polyisobutylene-containing adhesive matrix and pharmaceutically acceptable ingredients; and
c) optionally a removable release liner or protective layer.

In yet another embodiment a preferred application form consists essentially of
a) a backing layer,
b) an additional adhesive layer optionally comprising also an UV-absorber,
c) an intermediate layer impermeable to the UV-absorber or drugs such as e.g. steroidal hormones,
d) a polyisobutylene-containing adhesive matrix comprising Gestodene and Ethinylestradiol as the active ingredients,
e) optionally a removable release liner or protective layer.

Preferably, the backing layer, the polyisobutylene-containing adhesive matrix which contains Gestodene and Ethinylestradiol and the removable release liner (or protective layer) are transparent, which means that the skin is visible. The same applies to the additional adhesive layer and the intermediate layer which are transparent too.

In case the drug-containing polyisobutylene layer fails to exhibit sufficient self-tackiness to the skin, it may be provided with an additional layer of a pressure-sensitive adhesive layer or with a pressure-sensitive adhesive edge or ring so as to ensure adherence of the composition to the skin over the whole application period. The pressure-sensitive adhesive layer may be located between the drug-containing layer and the skin and the adhesive ring may be located around or at the edge of the drug-containing layer.

The size of the drug-containing polyisobutylene layer is selected from a variety of reasonable sizes. As used herein, a reasonable size is meant to be a surface area of from about 3 to 20 cm$^2$, preferably of from about 5 to 15 cm$^2$, most preferably of from about 7 to 12 cm$^2$, such as 10 or 11 cm$^2$. Notably, the surface area is the area that is in contact with or in close proximity to the skin or mucosa.

The composition comprises a drug-containing layer which comprises polyisobutylene and one or more pharmaceutically acceptable excipients or carriers and the drug-containing layer has solubility for Gestodene of no more than 3% by weight of the drug-containing layer as defined in EP 1 541 137 which is incorporated by reference and wherein the Gestodene is present in an amount ranging between 0.5 and 2% by weight of the drug-containing layer.

The phrase "solubility for Gestodene of no more than 3% by weight of the drug-containing layer" is meant to characterise the quantity of Gestodene that can dissolve in a particular drug-containing layer yielding a visually clear polymer matrix.

As used herein, the term "a Gestodene" is denoted to mean Gestodene (13beta-Ethyl-17alpha-ethynyl-17beta-hydroxy-4,15-gonadien-3-one).

The term "solubility for" should not be understood as meaning the actual concentration of Gestodene in the drug-containing layer. As described below, the total concentration of hormone in the drug-containing layer may be above or below 3% by weight of the drug-containing layer. Furthermore, the total concentration of hormone in the drug-containing layer may give rise to a drug-containing layer comprising the hormone at saturated or sub-saturated levels.

The term "drug-containing layer" is meant to denote that part of the transdermal composition or system wherein the steroidal hormones Gestodene and Ethinylestradiol are present. The drug-containing layer can be in semi-solid or solid form and comprises the hormones formulated directly in the layer. The hormones of the invention may be dispersed, partly dispersed, partly dissolved or fully dissolved in it dependent on the concentration and the physico-chemical properties of the hormones. The drug-containing layer is not meant to be in the form of a gel or a liquid. Intentionally, the drug-containing layer is meant to be in direct contact with the skin or mucosa. However, in some embodiments, there is an additional layer, a so-called nodrug-containing layer, located between the drug-containing layer and the skin or mucosa.

As said, compositions according to the invention do not necessarily comprise a skin penetration enhancer. Thus, in some embodiments of the invention, the drug-containing layer excludes the presence of a skin penetration rate enhancer, which means that the drug-containing layer consists essentially of ingredients not including a skin penetration rate enhancer. This means that for example less than 2%, such as less than 1%, preferably less than 0.5%, such as less than 0.2%, such as less than 0.1% by weight of the drug-containing layer is composed of a skin penetration enhancer.

The proper drug-containing layer is preferably made of a polyisobutylene or mixtures of polyisobutylene with other polymers. The polymers may have adhesive properties or may be without noticeable adhesive properties. In some embodiments, the drug-containing layer is a so-called pressure sensitive adhesive layer.

In principle any mixture of polymers resulting in the said solubility for Gestodene may be applied. Thus, in one embodiment of the invention the drug-containing layer comprises additionally at least one polymer that may have adhesive properties or not. Typically, such polymers are biologically acceptable lipophilic polymers of the types of a hydrocarbon polymer, a polysiloxane, a polyacrylate, or mixtures thereof. Preferably, the polymers may be selected from those hydrocarbon polymers, polysiloxanes and/or polyacrylates that form a drug-containing layer having solubility for Gestodene, of no more than 3% by weight of the drug-containing layer.

The amount of the polyisobutylene is to some extent a critical parameter. The proper amount may depend on the actual type of additional polymer and the steroidal hormones in use. In general, the amount of the polyisobutylene is at least 1% by weight of the drug-containing layer, such as at least 5%, 10%, 15% or 20%. However, preferably, polyisobutylene is present in the drug-containing layer in an amount of at least 25%, 30%, 35%, 40%, 45%, 50%, 55%, 60%, 65%, 70%, 75% or at least 80% by weight of the drug-containing layer. In other words, polyisobutylene can be used in an amount of from about 1 to 99% by weight of the drug-containing layer, such as from about 5 to 99%, 10 to 99%, 15 to 99% or 20 to 99%. Preferably, polyisobutylene is present in the drug-containing layer in an amount ranging from about 15 to 99%, such as from about 15 to 90%, 15 to 85% or 15 to 80%, such as from about 20 to 85%, 20 to 75%, such as from about 25 to 85%, 25 to 75% by weight of the drug-containing layer.

This being said, the invention is directed to a composition for transdermal delivery of Gestodene and Ethinylestradiol, the composition comprising a drug-containing layer that comprises Gestodene and one or more pharmaceutically acceptable ingredients or carriers;

polyisobutylene or a mixture of polyisobutylene with other polymers, preferably in an amount of from about 15 to 99% by weight of the drug-containing layer, wherein the polymer is being selected from hydrocarbon polymers, and mixtures thereof that form a drug-containing layer having a solubility with respect to Gestodene of no more than 3% by weight of the drug-containing layer.

The drug-containing layer may comprise as additional polymer a hydrocarbon polymer, which is selected from the group of polybutenes, polyisoprenes, polystyrenes, styrene isoprene styrene block polymers, styrene butadiene styrene block polymers and/or mixtures thereof.

As mentioned above, in some embodiments of the invention, the drug-containing layer is adhesive. Preferentially, the polymer of the drug-containing layer has suitable adhesive properties so that no further sticky agent, such as a tackifier is required. Whenever it is considered necessary to improve the adhesive strength of the drug-containing layer, the layer further comprises a tackifier.

The term "tackifier" denotes an agent that improves the adhesive strength of the adhesive layer to the skin or mucosa.

Examples of tackifiers are selected from hydrocarbon resins, rosin resins and terpene resins. Examples of hydrocarbon resins are commercially available under the tradename Escorez® from ExxonMobil; Regalite®, Piccotac® and Picco® from Eastman or Indopol® from BP. Examples of rosin esters suitable for transdermal systems according to the present invention include esters of hydrogenated wood rosin e.g. pentaerythritol ester of hydrogenated wood rosin, esters of partially hydrogenated wood rosin e.g. pentaerythritol esters of partially hydrogenated wood rosin, esters of wood rosin, esters of modified wood rosin, esters of partially dimerized rosin, esters of tall oil rosin, esters of dimerized rosin, and similar rosins, and combinations and mixtures thereof. Such rosin esters are commercially available under the tradenames Foral®, Foralyn®, Pentalyn®, Permalyn® and Staybelite®.

In a preferred embodiment of the invention, the drug-containing layer comprises a tackifier in the form of a rosin ester such as pentaerythritol ester.

It is generally considered that the tackifier can be present in any suitable amount as long as the said critical solubility of Gestodene in the drug-containing layer is not affected noticeable. Thus, a tackifier may be present in the drug-containing layer in an amount of from about 0.1 to 95%, such as 0.5% to 95%, such as 1% to 95% by weight of the drug-containing layer. That is to say that the tackifier can be present in an amount of from about 1% to 85%, 1 to 75%, 1 to 65%, 1 to 55%, 1 to 50%, 1 to 45%, 1 to 40% or more preferably of about 1 to 35% such as preferably 1 to 30%, more preferably 1 to 25%. Obviously, the amount of tackifier in the drug-containing layer may be critical to the solubility of Gestodene in the drug-containing layer. Thus, in still other embodiments of the invention, the tackifier is present in the drug-containing layer in an amount of up to 35%, such as of up to 30%. More preferably, the amount of tackifier is up to 25%, such as up to 20% or 15% by weight of the drug-containing layer.

It follows that a further particular aspect of the invention relates to a composition for transdermal delivery of Gestodene and Ethinylestradiol, the composition comprising a drug-containing layer consisting essentially of:

Gestodene and one or more pharmaceutically acceptable ingredient(s) and/or carrier(s);

polyisobutylene or a mixture of polyisobutylene with other polymers, preferably in an amount of from about 15 to 99% by weight of the drug-containing layer. As mentioned the drug-containing layer has a solubility for Gestodene as mentioned above; and a tackifier in an amount of up to 85% by weight of the drug-containing layer.

As being said, the drug-containing layer is to be composed of ingredients forming a layer wherein the solubility criterion for Gestodene is met. Preferably, this criterion is met when the drug-containing layer is mainly composed of Gestodene and Ethinylestradiol together with polyisobutylene and optionally a tackifier.

Furthermore, in some embodiments, the drug-containing layer does not comprise, or at least only comprise a restricted amount of crystallisation inhibitors like polyvinylpyrrolidone, cellulose polymers, such as methyl or ethyl cellulose derivatives or hydroxypropyl methyl cellulose, or mixtures thereof.

Also in some embodiments a solubiliser, such as dimethylisosorbide, is not present in the drug-containing layer or at least only present in a restricted amount.

By the term "restricted amount" is meant that the polymer or solubiliser in question is present in a concentration in the drug-containing layer of less than 10%, such as less than 8, 5, 3, 2, 1, 0.5 or 0.2% by weight of the layer.

As mentioned, it has been possible to provide sufficient skin penetration of the steroidal hormones Gestodene and Ethinylestradiol without incorporating a skin penetration enhancer and/or permeation enhancer. That is to say that in interesting embodiments of the invention, a skin penetration enhancer and/or permeation enhancer is excluded in the drug-containing layer or present in the drug-containing layer in a restricted amount, this amount being less than 5%, such as less than 4%, 3%, 2%, 1%, 0.5%, or 0.2% by weight of the drug-containing layer.

The terms "skin penetration enhancers" and "permeation enhancer" used in the present invention are meant to be interchangeable terms and denote compounds, which provide enhanced skin penetration/permeation to the active drugs when it is administered together with the drugs to the skin of a user. Penetration/permeation enhancers in transdermal formulations will change the thermodynamic activity of the drug in the drug-containing layer, and thereby lead to a positive or negative "push" effect. In addition, some penetration/permeation enhancers may conceivably penetrate into the highly ordered intercellular lipid structure of the stratum corneum and reduce its resistance by increasing lipid acyl chain mobility, thus providing a "pull" effect.

Any skin penetrating/permeation enhancing effect of a substance may be recognised upon testing identical formulations with and without penetration enhancer, for example by using nude mouse skin or the like. The skilled person knows such test methods.

Typical penetration/permeation enhancers are included in the group of compound listed below:

Alcohols, such as monohydric alcohols having about 2 to 10 carbon atoms, such as ethyl, isopropyl, butyl, pentyl, octyl, decyl and/or benzyl alcohols; dihydric alcohols such as 1,2-propanediol, polyhydric alcohols such as glycerin, sorbitol and/or polyethylene glycol; saturated and unsaturated fatty alcohols with 8-18 carbon atoms, such as capryl-, decyl-, lauryl-, 2-lauryl-, myristyl-, cetyl-, stearyl-, oleyl-, linoeyl- and linolenylalcohol.

Fatty acids, such as saturated or unsaturated fatty acids that may include 8-18 carbon atoms, for example, dodecanoyl acid, tetradecanoyl acid, stearoyl acid, oleic acid, linoleic acid, linolenacid and hexadecanoyl acid, triacetin, ascorbic acid, panthenol, butylated hydroxytoluene, tocopherol, tocopherol acetate, tocopheryl linoleate. Other fatty acids include but are not limited to valerian acid, capronic acid, capryl acid, pelargon acid, caprin acid, isovalerian acid, neopentan acid, neoheptan acid and/or isostearin acid.

Esters such as aliphatic esters ethyl acetate, lower ($C_1$-$C_4$) alkyl ester of lactic acid, fatty acid esters of the general formula $CH_3(CH_2)_n COOR$, wherein n is a number from 8 to 18 and R is an alkyl residue of maximally 6 carbon atoms, such as fatty acid esters for example, those of lauric acid, myristic acid, stearic acid and palmitic acid, e.g., the methyl esters, ethyl esters, propyl esters, isopropyl esters, butyl esters, sec-butyl esters, isobutyl esters of these acids, or dicarboxylic acid diesters of the general formula $R'OCO(CH_2)_m COOR'$, wherein m is a number from 4 to 8 and R' in each case means an alkyl residue of maximally 6 carbon atoms, such as propyl oleate, decyl oleate, isopropyl palmitate, glycol palmitate, glycol laurate, dodecyl myristate, isopropyl myristate and glycol stearate, suitable dicarboxylic acid diesters are, for example, the diisopropyl adipate, diisobutyl adipate and diisopropyl sebacate.

Ethers, such as polyethylene glycol ethers of aliphatic alcohols (such as cetyl, lauryl, oleyl and stearyl) including polyoxyethylene(4)lauryl ether, polyoxyethylene(2) oleyl ether and polyoxyethylene(10)oleyl ether.

Alkanes, such as alkanes with chain lengths of 6 to 17 carbon atoms.

Amides such as dimethyl acetamide, dimethyl formamide, dimethyl lauramide, dimethyl laurylamide and/or fatty acid amides and theirs derivatives.

Amides, such as amides with long aliphatic chains, or aromatic amides, urea and urea derivatives such as cyclic urea, dodecyl-urea, diphenyl-urea and/or allantoin.

Amino acids.

Amino acetates, such as derivatives of amino acetates such as dodecyl-N,N-dimethyl-aminoacetate and dodecyl-2-methyl-2-(N,N-methylaminoacetate), decyl-2-(N,N-dimethyl-amino)-propionate, decyl-2-(N,N-dimethylamino)-butyrate, octyl-2-(N,N-dimethylamino)-propionate, and/or docecyl-(N,N-dimethylaminophenylacetate.

Azone derivatives such as 1-dodecylazacycloheptane-2-one derivatives, azacycloalkanone derivatives and/or hexamethylenlauramide derivatives.

Cyclodextrins such as alpha, beta, and gamma cyclodextrins.

Glycerides, such as Monoglycerides, including glycerol monooleate, glycerol monolaurate and glycerol monolinoleate, polyethylene glycol-3-lauramide (PEG LR), polyethylene glycol monolaurate (PGML) glycerol monooleate (GMO), glycerol monolinoleate and/or glycerol monolaurate (GML).

Glycols such as ethylene glycol, diethylene glycol, or propylene glycol dipropylene glycol and/or trimethylene glycol.

Oils, such as mineral, vegetable, animal and fish fats and oils such as cotton seed, corn, safflower, olive and castor oils, squalene, and/or lanolin.

Polyols such as propylene glycol.

Pyrrolidones such as 2-pyrrolidone, N-methyl-2-pyrrolidone, dodecyl-pyrrolidone, 2-pyrrolidon-5-carboxylicacid, N-hexyl-, N-lauryl-, 4-carboxy-, 4-carboxycarbon derivatives, 3-hydroxy-N-methyl-2-pyrrolidon, N-farnesyl-2-pyrrolidon, N-(2(decylhio)ethyl)-2-pyrrolidone and/or N-(2-hydroxyethyl)-2-pyrrolidone.

Sulfoxides such as sulfoxide derivatives such as methyloctyl-sulfoxide, dimethylsulfoxide (DMSO), hexylmethylsulfoxide (hexyl-MSO) and/or decylmethyl-sulfoxide (decyl-MSO).

Surface active agents such as cationic surfactants like cetyltrimethylammonium bromide, octadecyltrimethylammoniumchloride, cetylpyridiniumchloride and/or equivalent cationic compounds, anionic surfactants such as sulphate salts which include but are not limited to compounds such as sodium lauryl sulphate and/or sodium dodecyl sulphate, and non-ionic surfactants such as esters of sorbitol and sorbitol anhydride which include but are not limited to polysorbate, sorbitanmonopalmiate and/or sorbitan-polyoleat.

Terpenes, ketones and oxides.

In addition to the steroidal hormones Gestodene and Ethinylestradiol, the polymer polyisobutylene or mixtures of polyisobutylene with other polymers, the one or more tackifiers, the drug-containing layer or other parts of the composition also contain stabilisers, dyes, pigments, inert fillers, anti-ageing agents, anti-oxidants, elastomers, thermoplastics and other conventional components of transdermal compositions that are known in the art. Preferably, the composition, or at least the drug-containing layer, does not comprise or does only comprise in a restricted amount (less than 1%, 0.8%, 0.5%, 0.2% or 0.1% by weight of the drug-containing layer) polyvinylpyrrolidone, methylcellulose, ethyl cellulose, hydroxypropyl methylcellulose, and/or dimethyl-isosorbide.

It should be understood that compositions of the inventions are transparent or at least in very interesting embodiments transparent, which means that the skin can be visually inspected through the drug delivery system. That is to say that the drug-containing layer is a monophasic system in which the drug (here Gestodene) is completely dissolved in the drug-containing layer.

The drug-containing layer is further characterised by being homogenous. The term "homogeneous" is used to describe a monophasic system, wherein the matrix is composed of one polymer phase. These systems can be distinguished from multiphase systems, which are composed of at least two polymer phases. In most cases multiphase systems can be detected visually by their opaque appearance. The opaque appearance is caused by the light diffraction due to differences in the diffraction index of the polymer phases. Other methods to detect monophasic systems are microscopic or rheological methods or by mechanical stretching thin polymer films. During mechanical stretching, the thin polymer film composed of multiphase systems turns opaque, as determined visually.

Thus, in summary it should be understood that interesting embodiments of the invention include:
a drug-containing layer that comprises:
i) Gestodene and Ethinylestradiol
ii) polyisobutylenes and
iii) the drug-containing layer comprises the Gestodene in an amount of 0.4 to 1.95%, preferably of from about 0.9 to 1.5% by weight of the drug-containing layer and Ethinylestradiol in an amount of from about 0.5% by weight of the drug-containing layer.

In further interesting embodiments thereof the drug-containing layer is characterised by the following parameters, which may be present as a single parameter or as mixture of parameters;

The drug-containing layer excludes dimethylisosorbide or contains an amount of dimethylisosorbide of less than 0.5% by weight of the layer;

The drug-containing layer excludes polyvinylpyrrolidone, methylcellulose, ethylcellulose and/or hydroxypropylcellulose or contains an amount of less than 2% by weight of the layer of polyvinylpyrrolidone, methylcellulose, ethylcellulose and/or hydroxypropylcellulose;

The drug-containing layer contains Gestodene and Ethinylestradiol completely dissolved in the layer;

The drug-containing layer is transparent;

The drug-containing layer is homogenous;

The drug-containing layer is monophasic;

The drug-containing layer excludes a skin penetration enhancer or contains an amount of less than 2% by weight of the layer;

The drug-containing layer comprises polyisobutylene in an amount of from about 15 to 99% by weight of the layer;

The drug-containing layer comprises a tackifier, such as a rosin ester, in an amount of up to 85% by weight of the drug-containing layer;

In a further embodiment of the invention an additional adhesive layer containing an UV radiation absorber is arranged between the backing layer and the drug-containing adhesive matrix which contains polyisobutylene and contains the active ingredients Gestodene and Ethinylestradiol.

The UV absorber is a Tinosorb or Tinuvin UV absorber, preferably Tinosorb S.

An intermediate or separation layer is arranged between the additional adhesive layer containing said UV absorber and the drug-containing layer. The separation or intermediate layer is impermeable to the active ingredients as well as to the UV absorber. Preferably the intermediate or separation layer is impermeable to Gestodene and Ethinylestradiol.

Resulting from this structure it is impossible that a contact occurs between the active ingredients and the UV absorber. The advantage of this setup is that the UV-absorber is contained only in the thin adhesive layer between the backing and intermediate layer, thus the required amount of UV-absorber in the formulation can be reduced compared to a systems, where the UV-absorber would be distributed over the whole drug containing adhesive matrix. Moreover, it is prevented, that the UV absorber is in direct contact to the skin. thus preventing potential side effects, such as e.g. allergic reactions of the skin.

Thus, one embodiment of the invention is set up according to the drawing in FIG. 1. FIG. 1 shows a cross-section of the patch with a backing layer A, adhesive layer B containing an UV absorber, intermediate or separation layer C, drug-containing adhesive matrix D and release liner E.

As mentioned above, the compositions of the invention are characterised by delivering a therapeutically effective contraceptive amount of Gestodene in combination with Ethinylestradiol. In other terms, the composition may be characterised by having a drug-containing layer delivering Gestodene in an amount of from 0 to 700 µg in 24 hours, preferably from 130-665 µg, preferably from 200-520 µg, most preferably from 360-520 µg in 24 hours and Ethinylestradiol in an amount of 40-220 µg in 24 hours, preferably 70-190 µg, preferably 100-165 µg, most preferably 135-140 µg in 24 hours.

Furthermore and as can be seen from table 3, the compositions of the invention are characterised by having a drug-containing layer delivering Gestodene in an amount of 600-665 µg, e.g. 600 µg or 630 µg or 660 µg and Ethinylestradiol in an amount of 120-135 µg, e.g. 120 µg or 130 µg or 135 µg or 520 µg Gestodene and 140 µg Ethinylestradiol or 350-380 µg Gestodene and 160-165 µg Ethinylestradiol or 200-210 µg, e.g. 205 µg Gestodene and 175-190 µg, e.g. 180 µg Ethinylestradiol or 210-230 µg, e.g. 215 µg or 230 µg Gestodene and 90-100 µg, e.g. 95 µg or 100 µg Ethinylestradiol or 290-350 µg, e.g. 295 µg or 350 µg Gestodene and 60-70 µg, e.g. 65 µg Ethinylestradiol.

The above-mentioned amounts were measured in an in-vitro dissolution test as described under the pharmacokinetic results.

As mentioned, the composition is effective in inhibiting ovulation in healthy women.

The second steroid hormone Ethinylestradiol is incorporated together with the Gestodene in the same drug-containing layer or is incorporated in a separate drug-containing layer free of Gestodene.

To achieve the therapeutically effective amount of hormone in the blood, the actual concentration of the drug in the drug-containing layer may be adjusted. Generally speaking, the drug-containing layer should contain some hormone in excess of the amount of hormone to be absorbed for achieving the therapeutically effective amount of the hormone. According to the present invention, this excess is small, such as the amount of hormone is less than 10 times the desired/required amount of hormone, preferably less than 5 fold. For example, it is also considered important to limit the amount of hormone so as to reduce the overall exposure of hormone to the user, e.g., when in contact to the skin or mucosa. Appropriate concentrations of Gestodene in the drug-containing layer are therefore from 0.4 to 1.95% by weight of the drug-containing layer whereas the concentration of Ethinylestradiol is about 0.5% by weight of the drug-containing layer. As mentioned, the total concentration of hormone, such as Gestodene may result in drug-containing layers comprising the hormone in saturated or sub-saturated levels. In a very interesting embodiment, the concentration of Gestodene in the drug-containing layer is from about 0.4 to 1.95%, preferably of from about 0.9 to 1.5% by weight of the drug-containing layer.

Ethinylestradiol is present in the drug-containing layer in an amount of 0.5% by weight of the adhesive layer.

Moreover, Gestodene is in a mass ratio to Ethinylestradiol in the range of from about 4:1 to 1:1, for example, a ratio of about 4:1, about 3:1, about 2:1 or about 1:1.

The following combinations shall illustrate the compositions according to the invention without limiting to those:

TABLE 1

| no | Size of the transdermal delivery system in cm² | Amount of Gestodene in mg in a polyisobutylene-containing layer | Amount of Ethinylestradiol in mg in a polyisobutylene-containing layer |
| --- | --- | --- | --- |
| 1 | 3 | 0.57 | 0.15 |
| 2 | 4 | 0.38 | 0.2 |
| 3 | 4 | 0.76 | 0.2 |
| 4 | 5 | 0.95 | 0.25 |
| 5 | 5 | 0.48 | 0.25 |
| 6 | 5.5 | 1.05 | 0.275 |
| 7 | 6 | 0.57 | 0.3 |
| 8 | 7 | 0.67 | 0.35 |
| 9 | 7 | 1.34 | 0.35 |
| 10 | 7.5 | 0.72 | 0.375 |
| 11 | 9 | 0.86 | 0.45 |
| 12 | 11 | 0.525 | 0.55 |
| 13 | 11 | 1.05 | 0.55 |

TABLE 1-continued

| no | Size of the transdermal delivery system in cm² | Amount of Gestodene in mg in a polyisobutylene-containing layer | Amount of Ethinylestradiol in mg in a polyisobutylene-containing layer |
|---|---|---|---|
| 14 | 11 | 1.575 | 0.55 |
| 15 | 11 | 2.1 | 0.55 |
| 16 | 12 | 2.3 | 0.6 |

It has surprisingly been found that relatively high plasma levels of Gestodene can be maintained for a prolonged period of time by administering a small amount of Gestodene formulated in a composition of the invention. Also surprisingly, it is found that the plasma profile and plasma levels of Gestodene, as resulting from the administration of Gestodene and Ethinylestradiol of the above mentioned formulations are effective in inhibiting the ovulation in a woman.

Therefore, further described is the use of a composition of the invention for the inhibition of ovulation in a female, such as a woman. When the medicament is administered, then a plasma concentration-time curve of Gestodene is achieved characterised by having average plasma levels of Gestodene over a period of 7 days ($C_{av}$) in a concentration of at least 0.5 ng/ml, as determined at steady state conditions. As follows, described is a method for inhibiting ovulation in a female, such as a woman, comprising administering topically to skin or mucosa an effective amount of Gestodene in combination with Ethinylestradiol, so as upon singly administering said Gestodene, then a plasma concentration-time curve of Gestodene is achieved characterised by having plasma levels of Gestodene in a concentration of at least 1.0 ng/ml, as determined at steady state conditions.

It has to be stated that the terms "plasma level" and "serum level" will be used interchangeably. With regard to drug concentrations of steroid hormones, there is no difference if they are measured in serum or plasma. When the term "plasma" is used, the same applies to "serum".

Alternatively, the uses and methods are for the treatment of other symptoms, disorders or symptoms which are normally treated by administering Gestodene and Ethinylestradiol. Therefore, it should in general be understood that the uses and methods are for the treatment of pain in endometriosis, premenstrual syndrome, climacteric disorders, regulating menstrual cycle and/or stabilising menstrual cycle.

Gestodene is administered in combination with Ethinylestradiol for the treatment of climacteric disorders, such as symptoms and diseases associated with menopause, such as hot flushes, sweating attacks, palpitations, sleep disorders, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition and/or osteoporosis. Most notably the treatment is directed to hot flushes, sweating attacks, palpitations, sleep disorders, mood changes, nervousness, anxiety, urogenital atrophy, and atrophy of the breasts or for the prevention or management of osteoporosis.

According to the present invention, the plasma concentration-time curve of Gestodene at steady state conditions is characterised by having mean values of average Gestodene plasma levels ($C_{av}$) in the range of Gestodene of 0.5-7.0 ng/mL, preferably 2.0-6.0 ng/mL, most preferably 3.5-6.0 ng/mL whereas the individual concentrations of the preferred range are in the range of 1-12 ng/ml. Correspondingly, during multiple dosing, the mean maximum Gestodene plasma levels ($C_{max}$) are about 0 to 10 ng/mL, preferably 3-9 ng/mL and the minimum Gestodene plasma levels ($C_{min}$) are about 0.5-4.5 ng/mL, preferably 2-4.0 ng/mL.

In a preferred embodiment, the plasma concentration-time curve of Gestodene at steady state conditions is characterised by having plasma levels of Gestodene in a concentration of about 4.2 ng/ml ($C_{av}$), such as about 4.9 ng/ml ($C_{max}$) or about 3.2 ng/ml ($C_{min}$). In other interesting embodiments, the plasma concentration-time curve of Gestodene at steady state conditions is characterised by having average concentrations of Gestodene in the range of 5 ng/ml, preferably in the range of 4.0 to 6.0 ng/ml following the first 6 days after single administration of a composition of Gestodene or a derivative thereof, preferably in the form of a composition of the invention.

The plasma concentration-time curve of Gestodene at steady state conditions is characterised by having maximal plasma levels of Gestodene in the period of 18 to 60 hours following repeated administration of the medicament and/or having plasma levels of Gestodene at steady state conditions in the period of 5 to 7 days following single administration of the medicament in the order of at least 50% of the maximal plasma levels of Gestodene obtained during the first 18 to 60 hours following administration.

The Gestodene/Ethinylestradiol-composition is preferably administered repeatedly in cycles of 28 days such that within each cycle of 28 days, the Gestodene/Ethinylestradiol-composition is administered with an interval of 7 days in a period of 21 days (3 weeks) followed by no administration of the Gestodene/Ethinylestradiol-composition for 7 days (one week). That is to say that the Gestodene/Ethinylestradiol-composition is administered on day 1, 8 and 15 within each cycle of 28 days. Preferably, said day 1 may be the day of the start of menstruation, or any other suitable day, such as the first, second, third, fourth, fifth or sixth day following the day of start of menstruation. In another embodiment, the Gestodene/Ethinylestradiol-composition, is administered repeatedly in cycles of 12 weeks such that within each cycle of 12 weeks, the Gestodene/Ethinylestradiol-composition is administered with an interval of 7 days in a continuous period of 11 weeks followed by no administration of Gestodene or a derivative thereof for 7 days (one week).

As may be understood, the uses and methods of the invention include the application of Gestodene/Ethinylestradiol-composition which may be in the form of a composition as defined herein. Thus, the term "medicament" includes a composition as defined herein. Furthermore, the term "medicament" is meant to include a kit of the invention.

In a still further aspect, the invention relates to a kit comprising 1 to 52, 1 to 26, 1 to 13 dosage units for application onto the skin over a period of 52, 26 or 13 weeks plus 7 days without a patch. A dosage unit is one patch for 7 days or one week. The application of that patch is always on day 1 of the first day of menstruation or day 2, 3, 4, 5 or 6. The application of the next patch starts 7 days after the application of the first patch, i.e. on day 8, 9, 10, 11, 12 or 13 after the first day of menstruation. The administration of the innovative patch can be for three times of 7 days, i.e. 21 days, with seven days break. That means three patches for three week and one week without a patch.

The administration can also be carried out for example over a period of 1 to 52, 1 to 26, and 1 to 13 weeks without a break. Other time periods within the mentioned ranges are possible. After the continuous administration of a number of patches over a long period of time, a break of 7 days has to be carried out.

Each dosage unit comprises Gestodene in a dose from about 0.38 to 2.3 mg, preferably 0.525 to 2.1 mg, more preferably 1.05 to 1.575 mg.

It is further to be understood that the kit further comprises Ethinylestradiol in a dose from about 0.15 to 0.6 mg, preferably 0.35 to 0.55 mg. Ethinylestradiol is combined together with the Gestodene in the same dosage unit or provided in separate dosage units.

Possible combinations of both hormones are illustrated in table 1.

The compositions of the invention may be fabricated using procedures known in the art. One example is included herein.

Example 1

Manufacturing of a Patch

A composition of the invention is prepared as described in EP1 541 137, example 1, except that tetrahydrofuran is used to dissolve the Gestodene and Ethinylestradiol.

The thus obtained patches have a size of 11 cm$^2$ and the following composition:
Gestodene: 1.05 mg
Ethinylestradiol: 0.55 mg
Polymer 108.4 mg
(in the form of polyisobutylene in combination with a tackifier e.g. MA-73B®)
Intermediate layer: 11 cm$^2$
UV-absorber: 0.825 mg
Polymer: 32.175 mg
Release liner: 11 cm$^2$
Backing layer: 11 cm$^2$ Other examples can be derived accordingly based on the compositions for Gestodene and Ethinylestradiol and the patch sizes given in tables 1 and 3.

Example 2

Pharmacokinetic Profile

The effect on ovulation inhibition, serum drug concentrations and safety of a patch of the invention was investigated in a selected population of women. The study design was based on the requirements of the EMEA guideline for clinical studies with contraceptive steroids (Committee for Proprietary Medicinal Products, CPMP/EWP 519/98).

Study Design

The study has three phases; a pre-treatment phase including one washout cycles and one additional cycle to ensure that the selected women were ovulatory. Finally, the second phase is a treatment phase of three cycles, which was followed by a third phase consisting of one-cycle post-treatment phase.

Women enrolled in the study were required to be healthy, non-pregnant, non-smoking, non-lactating female volunteers aged between 18 and 35 years, with a normal body mass index of 18-30 kg/m$^2$. Only women with light skin were included so that application sites could be easily and uniformly assessed.

Test patch C is a patch comprising a drug-containing layer of 0.55 mg Ethinylestradiol and 2.1 mg Gestodene and MA-73B®, the drug containing layer has a size of 11 cm$^2$. MA-73B® is a polyisobutylene based adhesive from Adhesive Research. Test patch D is identical to patch C but containing 0.55 mg Ethinylestradiol and 1.05 mg Gestodene.

During the study, blood was drawn for the determination of endogenous hormones, such as estradiol, progesterone, follicle stimulating hormone, sex hormone binding proteine, Ethinylestradiol, Gestodene. Transvaginal ultrasound examination was carried out to evaluate development of ovarian follicle-like structures. Patch adhesion, skin reactions at the application site and the woman's general health status was assessed. Vaginal bleeding was also evaluated.

During the pre-treatment cycle normal and spontaneous ovulation was established by assessment of serum progesterone values in that only women with an ovulatory pre-cycle and progesterone serum levels higher than 5 nmol/l were admitted to the treatment phase.

The treatment phase includes a period of three menstrual cycles. The first treatment in the first cycle began one day after the volunteers started menstruating in this cycle by application of a patch to the lower abdomen. Patches were applied to the clean, dry intact and preferably hairless skin of the lower abdomen, below the navel, starting with the right side in the first treatment cycle, and then alternating sides. A total of three test patches were applied in intervals of 7 days between, such as application at days 1, 8 and 15 of the first cycle. Each patch was worn for 7 days, and then replaced with a new patch to complete a total of 21 days of continuous use. This was followed by a 7-day treatment-free interval before the next treatment period started with a total of three patches applied, each applied with an interval of 7 days. If the patches were lost or became more than 50% detached, a new patch was applied.

Determination of Pharmacokinetic Variables

Serum concentrations of the estrogen and progestin, including Ethinylestradiol and Gestodene, were determined throughout the study to assess the pharmacokinetic characteristics of the patch. The sampling points were at the day 24 of the pre-treatment cycle and approximately every 3$^{rd}$ day during treatment cycle 2 as well as cycle 3. In addition, a daily sample was taken during week 3 of treatment cycle 3.

The concentrations of Ethinylestradiol and Gestodene were determined by conventional methods known in the art. Specifically, the concentration of Ethinylestradiol and Gestodene were determined by liquid chromatography using mass spectrometry as the detection method. The lower limits of quantification for Ethinylestradiol and Gestodene were 2.5 pg/ml and 50 pg/ml, respectively.

Pharmacokinetic data collected during the study is analyzed using nonlinear mixed effects models. Mixed effects models, or population-type pharmacokinetic models, describe the relationship between dose and time and variables such as drug plasma concentrations. Both structural and random effects are involved in this relationship. A population pharmacokinetic compartmental model is developed using the concentration of the drug as the dependent variable. Individual parameters like AUC during steady state based on the population pharmacokinetic model will be calculated. In addition, parameters like $C_{max}$, AUC (0-168 h), and $C_{min}$ are calculated during the 3$^{rd}$ week of cycle 3 by means of non-compartmental methods.

Results

The primary pharmacodynamic variable was the proportion of women with ovulation inhibition.

No cases of ovulation were found in both treatment groups throughout the study. Ovulation inhibition, defined as a Hoogland score lower than 6 (ovulation), was sufficient for all volunteers in the per protocol set throughout the study.

Progesterone concentrations were adequately suppressed below 2.5 nmol/l in each of the treatment cycles. Mean estradiol levels in the blood were under 20 pg/ml on all days on which a patch was applied.

The Hoogland score is a method for the assessment of ovulation inhibition known to the skilled person. For example, a detailed description of that method can be found in the database BioMed Central (www.biomedcentral.com) in a publication of Doris Heger-Mahn, "Use of transvaginal sonography and hormone measurements in gynecological trials".

With transvaginal sonography the inner female organs (uterus, ovaries, and vessels) can be depicted in a harmless and easy way. Close meshed examinations (e.g. every 3rd day) throughout the cycle allow for assessment of follicle size, ovulation, luteal phase, and endometrial transformation. With Doppler sonography the blood flow changes under hormonal influence can be assessed. Estradiol and progesterone are the main hormones to be examined. Estradiol is produced by the growing follicle and progesterone is correlated with the development and regression of the corpus luteum in the second cycle half. In addition FSH and LH can be assessed. Exceptionally the evaluation of inhibin A and B, prolactin, testosterone or DHEAS can be needed. Basically the main hormones can be determined with RIA technique and with immunoassays (e.g. ECLIA=electro-chemi-luminescence immunoassay). The variability of the hormone values is considerably depending on the intervals for blood sampling, the release conditions for these hormones, and the specificity and reliability of the testing systems.

Data from both methods can be summarized within the so-called Hoogland Score with classifies the activity of the follicle-like structures seen by TVS.

Pharmacokinetic Results

After administering the study medication, Ethinylestradiol and Gestodene serum concentrations were quantifiable in all subjects. See results in Table 2.

applied transdermally using formulations with a similar composition correlate with the amounts of such compounds. Furthermore, it is well within the expectations that the plasma levels of two compounds applied simultaneously do not interfere with each other.

Formulation AA which is example 3 of EP 1 541 137 is herein assumed to be a patch comprising 1.9 mg instead of 1.0 mg Gestodene as described in example 3. No description of manufacturing a patch with 1.0 mg Gestodene can be found in EP 1 541 137. Additionally, a search on the website www-.clinicaltrials.gov does not give a hint on a clinical trial with a patch comprising 1.0 mg Gestodene and 0.9 mg Ethinylestradiol, but information about trials with 1.9 mg Gestodene and 0.9 mg Ethinylestradiol. It is therefore to be assumed that the amount of Gestodene in example 3 of EP 1 541 137 is erroneous.

The results of these previously published data for formulation AA and A as described in EP 1 541 137 as example 3 and 4, are impressively confirmed by the results obtained with formulation C that has approx. 110% Gestodene content and only approx. 60% Ethinylestradiol content when compared to formulation AA. This was also reflected in the plasma levels: the plasma level of formulation C was by approx. 10% increased for Gestodene and was only 65-70% for Ethinylestradiol compared to the plasma levels achieved by formulation AA after multiple administrations (Table 2). Again, these results perfectly match the expectations of a skilled person in that the plasma levels correlate with the drug content and in that the plasma levels of two compounds applied simultaneously do not interfere.

TABLE 2

Overview of patch formulations and resulting plasma data

| Formulation | Content Gestodene mg | Ethinyl-estradiol mg | Patch Size cm$^2$ | Administration | Gestodene $C_{max}$ pg/ml | $C_{av}$ pg/ml | $C_{min}$ pg/ml | Ethinyl-estradiol $C_{max}$ pg/ml | $C_{av}$ pg/ml | $C_{min}$ pg/ml |
|---|---|---|---|---|---|---|---|---|---|---|
| AA (Example 3 EP 1 541 137) | 1.9 | 0.9 | 10 | SD - MD | 1564-4416 | 1150-3560 | 1540-2920 | 40-50 (45-50) | 32-36 | 26-28 |
| A (Example 4A EP 1 541 137) | 1.9 | 0.9 | 10 | SD | 2082* | — | — | 53 | — | — |
| B (Example 4B EP 1 541 137) | 1.33 | 0.67 | 10 | SD | 1995* | — | — | 45 | — | — |
| C | 2.1 | 0.55 | 11 | MD | 5180 | 4100 | 2790 | 31 | 22 | 14 |
| D | 1.05 | 0.55 | 11 | MD | 4980 | 4090 | 2770 | 51 | 33 | 21 |

$C_{max}$: Maximum concentration during the observation period
$C_{av}$: Average concentration during the observation period
$C_{min}$: Minimum concentration during the observation period
SD = single dose, MD = multiple dose (steady-state)
*The plasma levels of Gestodene obtained after application of formulation A and B might be slightly overestimated due to short wash-out periods before application of these formulations that possible resulted in a carry-over effect of Gestodene from preceding treatment period.
Carry over relates to SHBG (Sexual Hormone Binding Globulin) which is decreased to the starting point during 7 days. The Gestodene concentrations remain at high levels.

Comparable plasma levels were achieved for the formulation AA and A when administered as a single dose. For formulation B, which has a reduced Ethinylestradiol and Gestodene content of approx. 70% compared to formulation AA and A, slightly reduced plasma levels of both Gestodene and Ethinylestradiol were achieved as compared to formulation AA and A when administered as an single dose (Table 2). This is well within the expectations of a skilled worker who generally assumes that the plasma levels of each compound Formulation D has only 50% of the Gestodene-content but the same Ethinylestradiol-content when compared to formulation C.

Surprisingly, even though the Gestodene-content in the patch formulation D was decreased by 50% compared to formulation C, nearly the same plasma levels were achieved for both formulations for Gestodene. Moreover, although in both formulations C and D the Ethinylestradiol-content was the same, the formulation D resulted in nearly twice as high plasma levels for Ethinylestradiol as for formulation C($C_{max}$ (C): 32 pg/ml vs $C_{max}$ (D); 55 pg/ml).

Without wishing to be limited to a specific theory, the present inventors have surprisingly found means to combine the contents of both Gestodene and Ethinylestradiol in such a way that high plasma levels of both compounds can be achieved with comparably low contents of Gestodene and Ethinylestradiol in the patch.

The plasma level to be expected in a clinical study can be estimated by in-vitro methods. For the release of the drugs from a formulation in-vitro dissolution methods are established even in the Pharmacopoeia. The dissolution test is conducted as described in the USP <724> or Ph. Eur. 2.9.4. method 1—for transdermal patches in the paddle over disk setup. Dioxane (HPLC-quality)/water, purified in a ratio of 30+70 is used as dissolution medium (1000 ml) at a rotation speed of 50 rpm at 32+/−0.5° C. Samples of 1 ml each are withdrawn at predetermined time points (1, 4, 8 and 24 h) and analysed for drug content of Gestodene and Ethinylestradiol by standard HPLC methods on a reversed phase column.

The drug release rate in the in-vitro dissolution test of different patch formulations was therefore investigated and compared to the drug release rates of the formulations AA, A and C and D (Table 3).

The results show, that it is possible to cover a broad range of drug release rates by adjusting the concentration of Ethinylestradiol and Gestodene in the patch matrix. The ratio of Ethinylestradiol and Gestodene in the patch formulation can be selected in such a way to achieve a required drug release rate from the patch formulation and thus the required plasma levels for both drugs.

TABLE 3

Release rates of varying patch formulations in in-vitro dissolution

| Patch size Gestodene content, mg | | | | | | | | | | | | | |
|---|---|---|---|---|---|---|---|---|---|---|---|---|---|
| | | | | | | Gestodene release (24 h) µg | | | | | | | |
| Ethinyestradiol content, mg | 0 | 135 | 175 | 200-210 | 210-230 | 250 | 290-350 | 350-380 | 450 | 500-520 | 530-550 | 600-665 | 700 |
| Ethinyl-estradiol release (24 h) µg 40 | | | 3 cm² 0.57 0.15 | | | | | | | | | | |
| 50 | | | | | 4 cm² 0.76 0.2 | | | | | | | | |
| 60 | | 4 cm² 0.38 0.2 | | | | | 5 cm² 0.95 0.25 | | | | | | |
| 60-70 | | | | | | | 5.5 cm² 1.05 0.275 | | | | | | |
| 75 | | | 5 cm² 0.48 0.25 | | | | | | | | | | |
| 85 | | | | 6 cm² 0.57 0.3 | | | | | 7 cm² 1.34 0.35 | | | | |
| 90-100 | | | | | 7 cm² 0.67 0.35 | 7.5 cm² 0.72 0.375 | | | | | | | |
| 120-135 | | | | | | | 9 cm² 0.86 0.45 | | | 10 cm²* 1.9 0.6 | 11 cm²*** 2.1 0.55 | 12 cm² 2.3 0.6 | |
| 140-145 | | | | | | | | | | 11 cm² 1.575 0.55 | | | |
| 160-165 | | | | | | | | 11 cm²** 1.05 0.55 | | | | | |
| 175-190 | | | | | 11 cm² 0.525 0.55 | | | | | | 10 cm² 1.9 0.9 | | |
| 200-220 | 11 cm² 0 0.55 | | | | | | | | | | | | |

*Formulation A/AA
**Formulation D
***Formulation C
The data in the grey-shaded box is for comparison only.

The drug release rate of Ethinylestradiol in combination with varying amounts of Gestodene in a transdermal patch results in increasing release rates of Ethinylestradiol in direct correlation to decreasing amounts of Gestodene in the in-vitro dissolution test, despite the use of constant amounts of Ethinylestradiol in the formulations (FIG. 1). Moreover, the release rate of Gestodene relatively to its concentration in the formulation was also increased.

Figure 2:
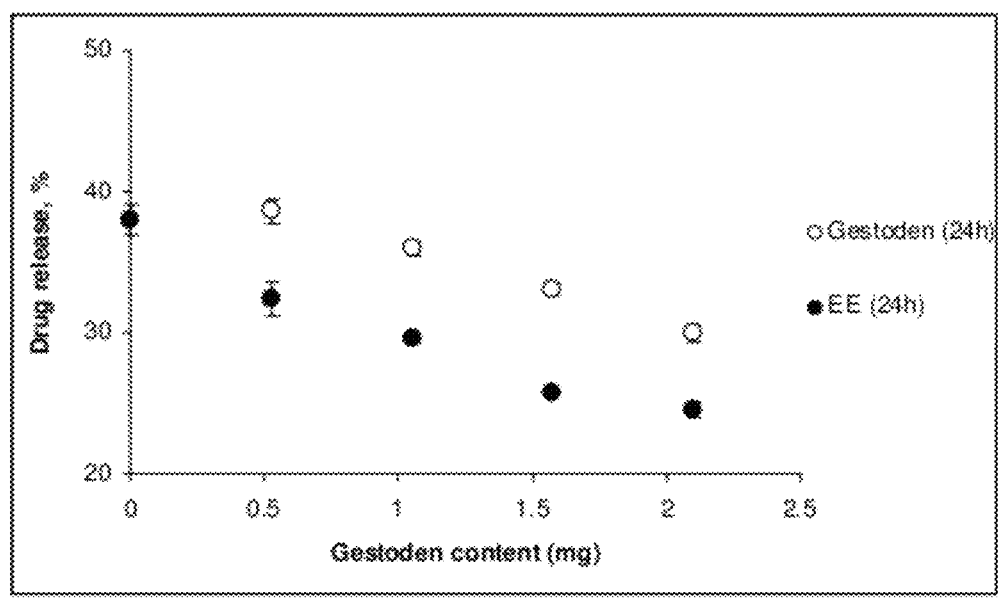
FIG. 2 shows the correlation of drug release from patches with varying concentration of Gestodene and constant concentration of Ethinylestradiol in the patch matrix (concentration of Gestodene between 0-1.9%; concentration of Ethinylestradiol 0.5%. Data were taken after 24 hours of in-vitro drug release of appropriate patches with a size of 11 $cm^2$).

FIG. 2 shows the correlation of drug release from patches with varying concentration of Gestodene and constant concentration of Ethinylestradiol in the patch matrix (concentration of Gestodene between 0-1.9%; concentration of Ethinylestradiol 0.5%. Data were taken after 24 hours of in-vitro drug release of appropriate patches with a size of 11 cm$^2$).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding EP application No. 10175498.4, filed Sep. 6, 2010, and EP application No. 11155469.7, filed Feb. 22, 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Transdermal therapeutic system containing, in order:
   a) a backing layer,
   b) at least one drug-containing adhesive layer comprising the active ingredients Gestodene and Ethinylestradiol in a polyisobutylene-containing matrix and optionally other pharmaceutically acceptable ingredients, and
   c) a release liner;
      wherein the Gestodene amount is from about 0.4 to 1.5% by weight of the drug-containing layer and the Ethinylestradiol amount is about 0.5% (w/w) by weight of the drug-containing layer.

2. Transdermal therapeutic system according to claim 1, wherein the transdermal therapeutic system contains an additional layer with an UV absorber between the backing layer and the drug-containing adhesive layer.

3. Transdermal therapeutic system according to claim 2, wherein the UV absorber is a Tinuvin or Tinosorb UV absorber.

4. Transdermal therapeutic system according to claim 3, wherein the UV absorber is Tinosorb S.

5. Transdermal therapeutic system according to claim 2, wherein the transdermal therapeutic system contains an additional intermediate or separation layer between the additional layer with an UV absorber and the drug-containing adhesive layer.

6. Transdermal therapeutic system according to claim 1, wherein the Gestodene amount is from about 0.9 to 1.5% by weight of the drug-containing layer.

7. Transdermal therapeutic system according to claim 1 containing, in order:
   a) a backing layer,
   b) an adhesive layer comprising a UV absorber,
   c) an intermediate layer which is impermeable to UV absorbers and/or the active ingredients Gestodene and Ethinyl Estradiol,
   d) at least one polyisobutylene-containing adhesive layer comprising the active ingredients Gestodene and Ethinylestradiol and pharmaceutically acceptable ingredients,
   e) a release liner.

8. Transdermal therapeutic system according to claim 1 containing Gestodene in an amount from about 0.38 to 2.3 mg.

9. Transdermal therapeutic system according to claim 1 containing Ethinylestradiol in an amount from about 0.15 to 0.6 mg.

10. Transdermal therapeutic system according to claim 1 having a size of 3 to 20 cm$^2$.

11. Transdermal therapeutic system according to claim 1 containing 1.575 mg Gestodene and 0.55 mg Ethinylestradiol or 1.05 mg Gestodene and 0.55 mg Ethinylestradiol or 0.525 mg Gestodene and 0.55 mg Ethinylestradiol with a size of 11 cm$^2$.

12. Transdermal therapeutic system according to claim 1 containing less than 5% of penetration enhancers.

13. Transdermal therapeutic system according to claim 1 containing dimethylisosorbide in an amount of less than 0.5% (w/w) by weight of drug-containing layer.

14. A method for contraception in women comprising administering a transdermal therapeutic system according to claim 1.

15. Transdermal therapeutic system according to claim 1 as a dosage unit for continuous administration over 7 days.

16. Kit comprising 1-52 dosage units as claimed in claim 15.

17. Transdermal therapeutic system according to claim 15 wherein the dosage unit has 0.525-2.1 mg Gestodene per dosage unit together with 0.55 mg Ethinylestradiol in a polyisobutylene-containing matrix with a size of 11 cm$^2$.

18. Transdermal therapeutic system according to claim 17, wherein the dosage unit contains 0.825 mg Tinosorb S.

19. Transdermal therapeutic system according to claim 17, wherein the dosage unit contains 1.05 to 1.575 mg Gestodene.

20. A transdermal delivery system of claim 1 containing Gestodene in an amount from about 0.525 to 2.1 mg.

21. A transdermal delivery system of claim 1 containing Gestodene in an amount from about 1.05 to 1.575 mg.

22. A transdermal delivery system of claim 1 containing Ethinylestradiol in an amount from about 0.35 to 0.55 mg.

23. A transdermal delivery system of claim 1 having a size of about 5 to 15 cm$^2$.

24. A transdermal delivery system of claim 1 having a size of about 8 to 12 cm$^2$.

25. A transdermal delivery system of claim 1 having a size of about 10 or about 11 cm$^2$.

* * * * *